United States Patent [19]

Kotick et al.

[11] 4,275,205

[45] Jun. 23, 1981

[54] 7,7-DITOSYLOXYMETHYL-4,5α-EPOXY-MORPHINAN-6-OLS

[75] Inventors: Michael P. Kotick; David L. Leland, both of Elkhart, Ind.

[73] Assignee: Miles Laboratories, Inc., Elkhart, Ind.

[21] Appl. No.: 146,384

[22] Filed: May 5, 1980

[51] Int. Cl.³ .................. C07D 489/02; A61K 31/485
[52] U.S. Cl. ........................ 546/44; 546/45; 424/260
[58] Field of Search .................. 546/45; 424/260; 546/44

[56] References Cited

U.S. PATENT DOCUMENTS 2,178,010  10/1939  Small et al. .................. 546/44 X

FOREIGN PATENT DOCUMENTS 2900918  8/1979  Fed. Rep. of Germany ........... 424/260

*Primary Examiner*—Donald G. Daus
*Assistant Examiner*—Diana G. Rivers

*Attorney, Agent, or Firm*—Jerome L. Jeffers

[57] ABSTRACT

Disclosed are 7,7-dimethyl-4,5α-epoxy-morphinan-6-one compounds characterized by the formula:

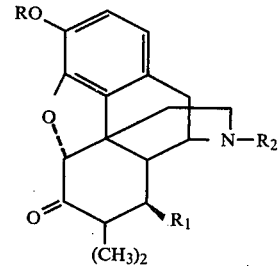

wherein R is H or $CH_3$, $R_1$ is H, $CH_3$ or $CH_2CH_3$ and $R_2$ is cyclopropylmethyl or cyclobutylmethyl. Particular compounds circumscribed by the foregoing formula are useful as analgesics, narcotic antagonists or mixed analgesics/narcotic antagonists.

4 Claims, No Drawings

7,7-DITOSYLOXYMETHYL-4,5α-EPOXY-MORPHINAN-6-OLS

BACKGROUND OF THE INVENTION

Certain well known narcotic analgesics belong to the class of 4,5α-epoxymorphinan compounds which have the following basic ring system, in which the atoms are numbered as indicated.

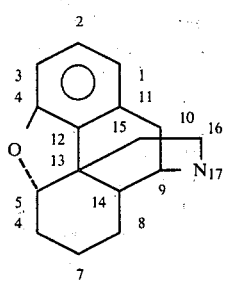

The two most familiar compounds of this class are morphine and its 3-methyl ether, codeine, with the structures indicated below.

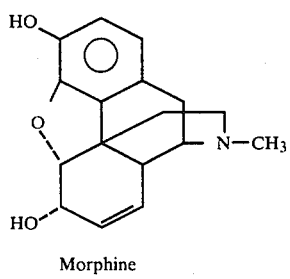

Morphine

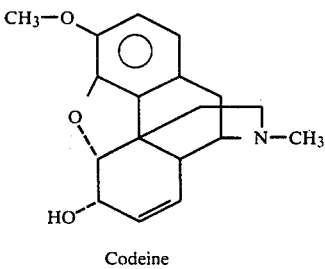

Codeine

When the 6-hydroxyl group of each of these compounds is oxidized to an oxo group, the compounds conveniently are referred to as morphinone and codeinone, respectively. When the N-methyl groups of the latter compounds are replaced by other substituent groups they may be referred to as N-substituted normorphinones and norcodeinones, respectively. There are two types of nomenclature commonly used for describing compounds herein. The trivial means, such as morphine or morphinone, are widely accepted and used for the sake of brevity and clarity. The Chemical Abstracts nomenclature is preferred and is used wherever precision is needed.

Morphine and its relatives are used primarily for the relief of pain (i.e., as analgesics). They are narcotic and possess dependence-inducing ability and produce other side effects that make them less than ideal analgesics (emesis, constipation, sweating, respiratory depressions, miosis). A compound with the appropriate profile of analgesic (agonist) and narcotic antagonist actions which is not morphine-like has potential as an analgesic agent for treatment of moderate to severe pain without liability of drug dependence. Furthermore, a compound having only strong narcotic antagonist action may be a desirable agent for treatment of drug dependence.

U.S. patent application Ser. No. 56,549, filed May 26, 1979 discloses 7, 8 and 7-8 substituted 4,5α-epoxymorphinan-6-one compounds of the formula:

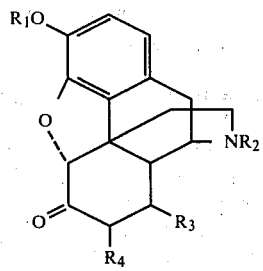

(II)

where $R_1$ can be H or methyl, $R_2$ can be cyclopropylmethyl, cyclobutylmethyl, allyl or tetrahydrofurfuryl, $R_3$ is H, methyl or ethyl and $R_4$ is H or methyl. Compounds disclosed in this application have analgesic activity, narcotic antagonist activity or a combination of these activities.

SUMMARY OF THE INVENTION

The present invention involves 7,7-dimethyl-4,5α-epoxymorphinan-6-one compounds characterized by the formula:

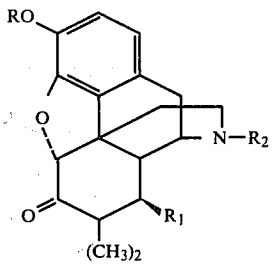

(III)

wherein R is H or $CH_3$, $R_1$ is H, $CH_3$ or $CH_2CH_3$ and $R_2$ is cyclopropylmethyl or cyclobutylmethyl provided that:

(a) when $R_1$ is H and $R_2$ is cyclopropylmethyl, R is H or $CH_3$ and when $R_1$ is H and $R_2$ is cyclobutylmethyl, R is H;

(b) when $R_1$ is $CH_3$ and $R_2$ is cyclopropylmethyl, R is H or $CH_3$ and when $R_1$ is $CH_3$ and $R_2$ is cyclobutylmethyl, R is H; and (c) when $R_1$ is $CH_2CH_3$, $R_2$ is cyclobutylmethyl or cyclopropylmethyl and R is H.

DETAILED DESCRIPTION

The compounds disclosed and claimed herein are prepared by the method set out in Scheme (I), infra. Referring to Scheme (I), reaction of dihydrocodeinone (1a) with formaldehyde, in the presence of calcium hydroxide in 1:2 methanol-water gave a dihydroxymethylated derivative (2a) which was isolated as the hydrochloride salt in good yield. The 8β-alkylated dihydrocodeinones (1b, c) when treated with formaldehyde under the same conditions, gave the desired (2b, c)

together with a second product which was identified as (3b, c) by Nuclear Magnetic Resonance (NMR) spectroscopy which indicated the presence of an extra methoxyl group at about 3.4δ. The amount of (3b, c) formed was found to be dependent upon the amount of methanol in the reaction mixture. For example, in 50% aqueous methanol, (1c) gave an approximately 1:10 mixture of (2c) and (3c), while in water containing 15% methanol, about a 1:1 mixture was obtained. An attempt to obtain (3a) from (1a), using methanol containing only a small amount of water as the reaction media, was unsuccessful. Formation of (3b, c) could be avoided by utilizing aqueous dioxane as the solvent for the condensation reaction.

Reaction of (2) with three equivalents of tosyl chloride in pyridine solution for several days gave mainly the disubstituted compounds (4) which were difficult to obtain in a pure state. Displacement of the tosyl groups in (4a) with lithium triethylborohydride proceeded slowly to give a good yield of the 7,7-dimethyl-6α-hydroxy compound (6a). Treatment of the 8β-alkyl derivatives (4b, c) under the same conditions quickly gave new products which were identified as the 7α-methyl-6β,7β-epoxymethylene compounds (5b, c). The epoxymethylene derivative (5a) can be obtained from (4a) by conducting the reaction with LiEt$_3$BH in refluxing tetrahydrofuran for short time periods.

Reductive cleavage of the strained 6,7-epoxymethylene bond in (5b, c) was accomplished by use of a 3:1 mixture of lithium aluminum hydride-aluminum chloride in refluxing ether for 24 to 36 hours. There was no indication for scission of the 4,5α-epoxy bond under these conditions. The resulting 7,7-dimethyl-6β-hydroxy compounds (6) were cleanly oxidized to the corresponding C$_6$-ketones (7) by use of dimethylsulfoxide-trifluoroacetic anhydride at −60° C. The insolubility of (6c) in methylene chloride necessitates the use of toluene as a co-solvent.

The N-methyl compounds (7a–c) were converted to the N-cycloalkylmethyl derivatives (10,11a–c) via the N-CN and N-nor compounds (8,9a–c). The 3-methoxy function was cleaved to give the 3-phenols (12a–c to 14a–c) by the use of either refluxing 48% hydrobromic acid or boron tribromide in chloroform solution at room temperature.

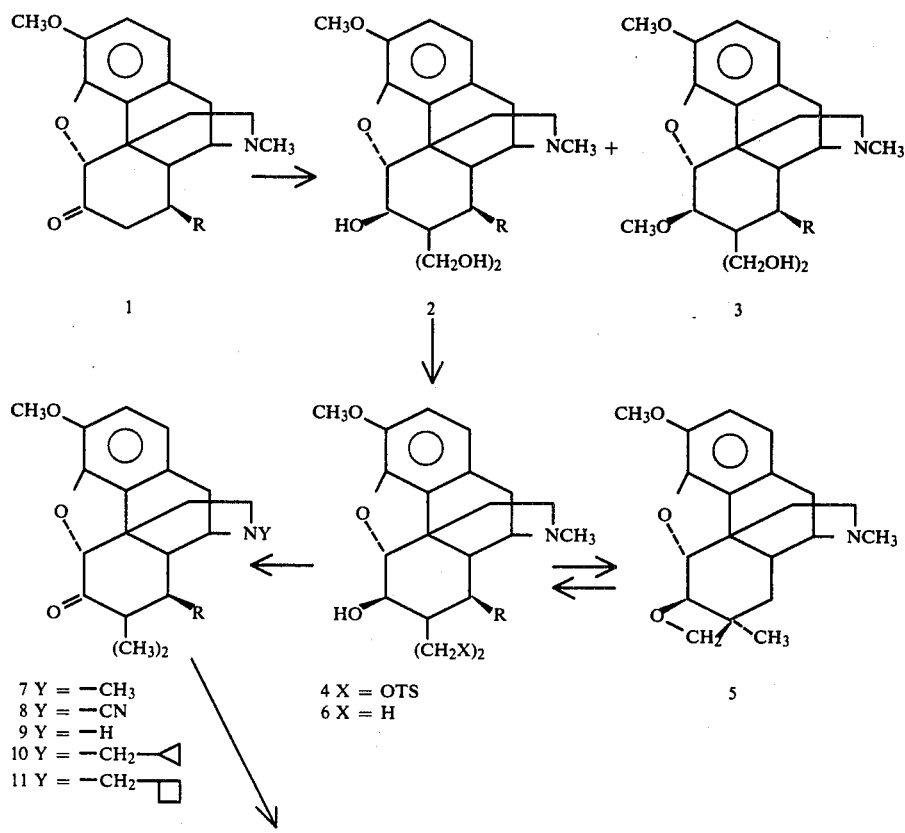

SCHEME (I)

-continued

SCHEME (I)

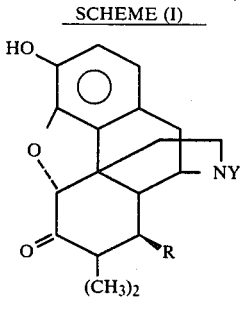

| | | |
|---|---|---|
| 12 Y = —CH₃ | | a series, R = —H |
| 13 Y = —CH₂—◁ | | b series, R = —CH₃ |
| 14 Y = —CH₂—▢ | | c series, R = —CH₂CH₃ |

The method of preparing the compounds of this invention and their pharmacology are further illustrated by the following examples. For these examples the term "processing in the usual manner" means that the organic phases were washed with dilute NH₄OH, dried (MgSO₄) and evaporated at 40° C. The residue was further dried at 50° C. under high vacuum. Column chromatography was performed over Silica Gel G using CHCl₃-MeOH mixtures (2:1 to 15:1) containing 2.0 to 0.5% concentrated NH₄OH. NMR spectra were determined in CDCl₃ unless otherwise noted.

EXAMPLE I

A.

7,7-Dihydroxymethyl-4,5α-epoxy-3-methoxy-17-methyl-morphinan-6β-ol (2a)

To a solution of 4,5α-epoxy-3-methoxy-17-methyl-morphinan-6-one (1a, 30.0 g, 0.10 mole) in dioxane (500 ml) was added H₂O (600 ml), Ca(OH)₂ (14.0 g. 0.19 mole) and 37% w/w formaldehyde solution (140 ml, 1.86 mole). The mixture was stirred at room temperature overnight and then concentrated under reduced pressure. The residue was diluted with H₂O and extracted with EtOAc. Processing in the usual manner gave a white foam which was converted to the HCl salt. Crystallization from aqueous EtOH gave 28.7 g (72%) of 2a in three crops. Recyrstallization from aqueous EtOH gave pure 2a. HCl, mp>265°. Elemental analysis was consistent with this formula.

B. 7,7-Dihydroxymethyl-8β,17-dimethyl-4,5α-epoxy-3-methoxy-morphinan-6β-ol (2b)

A solution of 1b (31.4 g, 0.10 mole) in dioxane (600 ml)—H₂O (600 ml) containing Ca(OH)₂ (14.0 g) and 37% formaldehyde solution (140 ml) was stirred overnight at room temperature and then evaporated to a small volume. Dilution with water was followed by extraction with ethyl acetate (EtOAc) and processing in the usual manner gave a foam. A combination of crystallization and chromatography gave 29.2 g (78%) of crystalline 2b. Recrystallization from ethanol (EtOH) gave analytically pure 2b as the hemi-hydrate, mp 109°–111°.

C.

7,7-Dihydroxymethyl-4,5α-epoxy-8β-ethyl-3-methoxy-17-methyl-morphinan-6β-ol (2c)

Compound 1c was reacted with formaldehyde in the presence of Ca(OH)₂ in dioxane-H₂O as indicated above for 24 hours and the reaction mixture processed as described. A portion of the resulting foam was converted to the HCl salt which crystallized from aqueous EtOH to give pure 2c.HCl mp>265°.

EXAMPLE II 7,7-Ditosyloxymethyl-4,5α-epoxy-3-methoxy-17-methyl-morphinan-6β-ols (4a–c)

A solution of 2a (35.7 g, 97 mmole) in dry C₆H₅N (200 ml) was cooled in an ice-salt bath and p-toluenesulfonyl chloride (pTsCl) (55.4 g, 290 mmole) added portionwise. The dark solution was then stirred at room temperature for 1 to 2 days, quenched by the addition of water and evaporated to a small volume. The residue was diluted with H₂O and extracted with chloroform (CHCl₃). The CHCl₃ extracts were processed to give a dark syrup which was chromatographed. Fractions containing the desired product were pooled to give 51.6 g (78%) of 4a as a tan foam whose structure was confirmed by NMR. Compounds 4b (66%) and 4c (56%) were prepared in a similar manner using the appropriate starting material and isolated as foams.

EXAMPLE III

A.

4,5α-Epoxy-6β,7β-epoxymethylene-3-methoxy-7α,8β-17-trimethyl-morphinan(5b)

To a solution of 4b (35.5 g, 51.9 mmole) in THF (425 ml) cooled in an ice-salt bath under argon was added dropwise, lithium triethylborohydride (LiEt₃BH) (208 ml of a 1 M solution in THF). The mixture was removed from the bath and stirred at ambient temperature for 3 hours. After cooling, the excess of hydride was destroyed by the addition of H₂O (25 ml). Following the dropwise addition of 3 N NaOH (50 ml) and 30% H₂O₂ solution (50 ml), the mixture was refluxed for 2 hours. The solution was cooled, the layers separated and the aqueous phase washed with CHCl₃. The combined organic phases were evaporated and the residue chromatographed to yield 15.8 g (89%) of crystalline 5b. Recrystallization from EtOAc gave pure 5b, mp 161°–162.5°. Elemental analysis and NMR spectra were consistent with the assigned structure.

B.

7α,17-Dimethyl-4,5α-epoxy-6β,7β-epoxymethylene-8β-ethyl-3-methoxy-morphinan (5c)

A solution of 4c (62.7 g, 90 mmole) in THF (800 ml) was reacted with LiEt₃BH (360 mmole) as above for 3 hours and the excess of hydride destroyed with $H_2O$ (40 ml). After refluxing with 3 N NaOH (80 ml) and 30% $H_2O_2$ (80 ml), processing gave a syrup which was chromatographed to give 24.5 g (77%) of 5c as a glass. Crystallization from ether gave pure material, mp 144°–146°. Elemental analysis and NMR spectra were consistent with the assigned structure.

EXAMPLE IV

A.
4,5α-Epoxy-3-methoxy-7,7,17-trimethylmorphinan-6β-ol (6a)

A solution of 4a (41.4 g, 61.7 mmole) in THF (400 ml) was cooled in an ice bath under an argon atmosphere and then treated dropwise with $LiEt_3BH$ (250 mmole). The mixture was stirred for 6 hours after which water (100 ml) was added cautiously to the cooled solution. To this clear solution was added 3 N NaOH (100 ml) followed by 30% $H_2O_2$ solution (100 ml). The mixture was refluxed for 2 hours, cooled and the layers separated. The aqueous layer was extracted twice with $CHCl_3$ and the combined organic extracts evaporated to give 22.2 g of 6a as a foam whose structure was confirmed by NMR. A portion of this foam was converted to the HCl salt which was twice crystallized from MeOH-EtOAc to give 6a.HCl, mp>265°.

B.
4,5α-Epoxy-3-methoxy-7,7,8β,17-tetramethyl-morphinan-6β-ol (6b)

To a suspension of $AlCl_3$ (6.17 g, 46.3 mmole) in diethyl ether ($Et_2O$) (500 ml) stirred in an ice bath under argon was added portionwise lithium aluminum hydride ($LiAlH_4$) (5.27 g, 139 mmole). The mixture was stirred for 30 minutes in the cold after which a solution of 5b (15.8 g, 46.3 mmole) in $Et_2O$ (1 L) was added. The mixture was refluxed for 24 hours, cooled and water added cautiously. The mixture was made basic with 3 N NaOH and filtered through Celite. The organic phase of the filtrate was separated and the aqueous phase extracted twice with $CHCl_3$. The combined organic phases were evaporated to give 15.3 g. (96%) of crystalline 6b. Two recrystallizations from $CHCl_3$-hexane gave 6b as the $CHCl_3$ solvate, mp 110°–112°.

C.
4,5α-Epoxy-8β-ethyl-3-methoxy-7,7,17-trimethyl-morphinan-6β-ol (6c)

A mixture of $AlCl_3$ (8.0 g, 60 mmole) and $LiAlH_4$ (6.8 g, 180 mmole) was prepared in $Et_2O$ (600 ml) as described above. To this was added 5c (21.3 g, 60 mmole) in $Et_2O$ (1 L) and the mixture refluxed for 36 hours. Processing as described gave a foam. Crystals of 6c (10.0 g) as the $CHCl_3$ solvate, mp 104°–108°, were obtained from $CHCl_3$-hexane. An additional 2.7 g of 6c (50% overall yield) was obtained by processing the mother liquor.

EXAMPLE V

A.
4,5α-Epoxy-3-methoxy-7,7,17-trimethyl-morphinan-6-one (7a)

To a solution of dimethylsulfoxide (DMSO) (6.3 ml. 88 mmole) in $CH_2Cl_2$ (80 ml) under argon cooled in a dry ice-acetone bath was added slowly, dropwise, trifluoroacetic anhydride (9.3 ml, 66 mmole) in $CH_2Cl_2$ (35 ml) while keeping the temperature below −60°. To this was added 6a (14.5 g, 44 mmole) in $CH_2Cl_2$ (80 ml) slowly, dropwise, so that the temperature remained below −55°.

The mixture was stirred in the bath for 90 minutes after which triethylamine (TEA) (18 ml, 245 mmole) was added dropwise. The mixture was allowed to warm to room temperature and extracted twice with $H_2O$. Evaporation of the organic phase gave a residue which was purified by chromatography to give 14.9 g of 7a as a glass whose structure was confirmed by NMR. A portion of this material was converted to the HCl salt which was also obtained as a foam and confirmed by elemental analysis.

B.
4,5α-Epoxy-3-methoxy-7,7,8β,17-tetramethyl-morphinan-6-one (7b)

Compound 6b (710 mg, 2 mmole) in $CH_2Cl_2$ (10 ml) was oxidized using DMSO (0.35 ml. 5 mmole) and trifluoroacetic anhydride (0.70 ml, 3.75 mmole) in methylene chloride ($CH_2Cl_2$) (8 ml) at −65° as described above. After the addition of TEA (1 ml), workup gave a residue which was purified by chromatography to give 474 mg (67%) of 7b as a glass whose structure was confirmed by NMR. This material was converted to the HCl salt which crystallized from methanol-ethyl acetate (MeOH-EtOAc) to give analytically pure 7b.HCl, mp 246°–248° which was confirmed by elemental analysis.

C.
4,5α-Epoxy-8β-ethyl-3-methoxy-7,7,17-trimethyl-morphinan-6-one (7b)

Prepared by oxidation of 6c (22.6 mmoles) in toluene (200 ml), using DMSO (45.2 mmoles) and trifluoroacetic anhydride (33.9 mmoles) in $CH_2Cl_2$ (50 ml), for 90 minutes at dry ice-acetone bath temperature. Workup by the addition of TEA (5 ml) followed by processing in the usual manner gave a foam which crystallized from EtOAc to give analytically pure 7c, mp 154°–156°.

EXAMPLE VI

17-Cyano-7,7-dimethyl-3-methoxy-morphinan-6-ones (8a–c)

To a rapidly stirred mixture of 7 (1.0 equivalents) in $CHCl_3$ (1 g in 15 ml) containing powdered $K_2CO_3$ (1.5 equivalents) was added dropwise a solution of BrCN (1.2 equivalents) in chloroform (1 g in 15 ml). The mixture was refluxed for two hours, cooled and the insoluble material removed by filtration. The filtrate was evaporated to dryness and coevaporated with EtOH until crystals formed. After cooling, the crystals were collected and hydrolyzed as indicated below. 8a, 77% yield, mp 194°–197°; 8b, 76%, mp 160°–162°; 8c, 79%, mp 195°–198°.

EXAMPLE VII 7,7-Dimethyl-3-methoxy-morphinan-6-ones (9a–c)

A suspension of 8 in 2 N HCl (1 g in 15–25 ml) was refluxed for 5 to 7 hours. The solution was cooled and the nor.HCl salt collected. This was used as is or converted to the free base for subsequent use in alkylation reactions as described below. 9a.HCl, 76%, mp>265°; 9b.HCl, 86%, mp>265°; 9c.HCl was obtained as the glassy free base in 97% yield by extraction from aqueous solution after the addition of concentrated $NH_4OH$.

EXAMPLE VIII

N-Cycloalkylmethyl-7,7-dimethyl-4,5α-epoxy-3-methoxymorphinan-6-ones (10a–c, 11a–c)

A mixture of 9 (free base or HCl salt) in dimethylformamide (DMF)(1 g in 20 ml) with NaHCO$_3$ (2.5 equivalents) and cycloalkylmethyl bromide, (1.2 equivalents) was heated in an oil bath at 100° under argon. Reactions utilizing the free base usually required 3 to 4 hours for completion while those employing the HCl salt were carried out for 16 to 22 hours. The cooled mixture was filtered to remove insolubles and the filtrate evaporated using an oil pump with a bath temperature of 50° C. The residue was dissolved in H$_2$O, the solution adjusted to pH 10–11 with concentrated NH$_4$OH and extracted with three portions of toluene. The organic phase was evaporated and the residue processed as described.

A.
17-Cyclopropylmethyl-7,7-dimethyl-4,5α-epoxy-3-methoxy-morphinan-6-one (10a) (TR-5385)

The residual foam (90%) was twice crystallized from EtOAc to give pure 10a, mp 146.5°–147.5°.

B.
17-Cyclopropylmethyl-4,5α-epoxy-3-methoxy-7,7,8β-trimethyl-morphinan-6-one (10b) (TR-5458)

The glass obtained (99%) was crystallized from EtOH to give 10b, mp 127°–128°, containing 0.25 mole of water which was confirmed by elemental analysis.

C.
17-Cyclopropylmethyl-7,7-dimethyl-4,5α-epoxy-3-methoxy-8β-ethyl-morphinan-6-one (10c) (TR-5443)

This compound was obtained as a glass in 88% yield. Both the HCl and tartrate.hydrate salts were obtained as foams.

D.
17-Cyclobutylmethyl-7,7-dimethyl-4,5α-epoxy-3-methoxy-morphinan-6-one (11a) (TR-5386)

The glass obtained in 72% yield was twice crystallized from EtOH to give pure 11a, mp 155°–156°.

E.
17-Cyclobutylmethyl-4,5α-epoxy-3-methoxy-7,7,8β-trimethyl-morphinan-6-one (11b) (TR-5462)

Evaporation of the toluene solution gave crystals which were twice crystallized from 95% EtOH to give 11b as needles, mp 163°–164°.

F.
17-Cyclobutylmethyl-7,7-dimethyl-4,5α-epoxy-3-methoxy-8β-ethyl-morphinan-6-one (11c) (TR-5442)

The toluene solution on evaporation gave an 85% yield of a glass. The HCl salt of 11c resisted crystallization and was obtained as a foam on evaporation from EtOAc.

EXAMPLE IX 7,7-Dimethyl-3-hydroxy-morphinan-6-ones (12a–c, 13a–c, 14a–c)

Method A

A suspension of the 3-methoxy compound in 48% HBR (1 g in 10 ml) was placed in a preheated 140° oil bath and the mixture refluxed for 15–20 minutes. The cooled solution was diluted with H$_2$O and then made basic by the addition of concentrated NH$_4$OH and extracted with three portions of EtOAc. The EtOAc extracts were evaporated and the residue purified by chromatography.

Method B

To a stirred solution of BBr$_3$ (40 mmole) in CHCl$_3$ (50 ml) under argon cooled to 0° was added the 3-methoxy compound (6.60 mmole) in CHCl$_3$ (50 ml). The mixture was stirred for 30 minutes at ambient temperature, recooled to 0° and MeOH (10 ml) added slowly, dropwise. The solution was evaporated to a small volume and diluted with H$_2$O. Concentrated NH$_4$OH was added and the mixture extracted with three portions of CHCl$_3$. The organic extracts were further processed in the usual fashion and evaporated to a residue which was chromatographed.

A.
7,7,17-Trimethyl-4,5α-epoxy-3-hydroxy-morphinan-6-one (12a)

Prepared by Method A. Chromatography yielded 89% of a tan foam which crystallized from MeOH-EtOAc to give pure 12a, mp 251.5°–253.5°.

B.
7,7,17-Trimethyl-4,5α-epoxy-8β-ethyl-3-hydroxy-morphinan-6-one (12c)

Prepared by Method B and obtained in 73% yield after chromatography. Conversion to the HCl salt followed by crystallization from MeOH-EtOAc gave pure 12c.HCl, mp>265°.

C.
17-Cyclopropylmethyl-4,5α-epoxy-7,7-dimethyl-3-hydroxy-morphinan-6one (12a) (TR-5388)

Prepared by Method A and obtained as crystals in 44% yield. Recrystallization from MeOH-EtOAc gave pure 13a, mp 252°–255°.

D.
17-Cyclopropylmethyl-4,5α-epoxy-3-hydroxy-7,7,8β-trimethyl-morphinan-6-one (13b) (TR-5461)

The free base of 13b was prepared by Method B and obtained as a foam in 72% yield. The hemi-d-tartrate salt, mp 240°–242°, was purified by crystallization from aqueous EtOH.

E.
17-Cyclopropylmethyl-7,7-dimethyl-4,5α-epoxy-8β-ethyl-3-hydroxy-morphinan-6-one (13c) (TR-5449)

Obtained by Method B as the glassy free base in 78% yield after chromatography. This was converted to the d-tartrate salt which was recrystallized twice from MeOH-EtOAc to give the mono-EtOAc solvate tartrate salt, mp 165°–180°.

F.
17-Cyclobutylmethyl-7,7-dimethyl-4,5α-epoxy-3-hydroxy-morphinan-6-one (14a) (TR-5390)

Prepared by Method A. The free base was obtained in 64% yield after chromatography. An analytical sample of the hygroscopic HCl salt of 14a, mp sinters 228°, melts 255° with dec., was obtained by two crystallizations from MeOH-EtOAc.

G. 17-Cyclobutylmethyl-4,5α-epoxy-3-hydroxy-7,7,8β-trimethyl-morphinan-6-one (14b) (TR-5449)

Obtained in 88% yield as a foam when prepared by Method B. This was twice crystallized from EtOAc to give analytically pure 14b, mp 195°–196°.

H. 17-Cyclobutylmethyl-7,7-dimethyl-4,5α-epoxy-8β-ethyl-3-hydroxy-morphinan-6-one (14c) (TR-5450)

The free base was obtained in 72% yield by use of Method B. The hygroscopic HBr salt of 14c was recrystallized twice from MeOH-EtOAc and had mp>265°.

PHARMACOLOGICAL EVALUATION

The compounds whose preparation is disclosed in the foregoing examples were screened to determine the following biological activities:

(A) Analgesic effects upon mice (acetic acid writhing test).

(B) Narcotic antagonist activity in rats (modified rat tail flick test).

TEST A. ACETIC ACID MOUSE WRITHING TEST

The analgesic effects of test compounds were determined in mice by use of the acetic acid writhing test described by B. A. Whittle, Brit. J. Pharmacol., 22:246 (1964). In this test at least three groups of five male CD-1 mice each were given subcutaneous doses of the test drug dissolved in either distilled water or distilled water acidified with HCl depending on the solubility of the compound. In all cases, 0.4 milliliter of a 0.5% V/V acetic acid in distilled water solution was administered intraperitoneally 15 minutes post drug. The number of writhes in a 20 minute interval beginning 5 minutes after the acetic acid injection were determined and compared with the number of writhes in control groups which had received only acetic acid.

Percent inhibition of writhing was calculated as:

$$\% \text{ inhibition} = \frac{\text{No. control writhes} - \text{No. treated writhes}}{\text{No. control writhes}}$$

The $ED_{50}$ dose, i.e., the dose required to reduce the number of writhes by 50%, was determined graphically from a plot of % inhibition as a probit versus log dose. Confidence limits of 95% were calculated on the basis of those results falling in the range 16–84% inhibition. See Litchfield, J. T., and Wilcoxon, F., J. Pharmacol. Exp. Ther., 96:99, (1949).

TEST B. EVALUATION OF NARCOTIC ANTAGONIST ACTIVITY

The narcotic antagonist effects of test compounds were determined by a modification of the rat tail flick procedure of Harris and Pierson, J. Pharmacol. Exp. Ther. 143:141 (1964).

Male albino Wistar rats (100–120 g) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp is used to adjust the intensity of the light falling on the tail of the rat such that the rat's control reaction time is from two to four seconds. Animals with a control reaction time outside this range are rejected. The rheostat adjustment is made only if a significant proportion (more than 2 out of every 10 rats) of the reaction times are outside the range of two to four seconds. Groups of five rats were used each time, and two control times were determined at 60 and 30 minutes prior to subcutaneous injection of the drug. A ten second cutoff time is employed; if the rat does not flick its tail in 10 seconds it is removed from the heat source.

Thirty minutes after the last control run the test drug was given interperitoneally. This was followed ten minutes later by an $ED_{80}$ dose of morphine subcutaneously. The animals were retested at 20 minutes after the morphine injection. Control animals were given vehicle and morphine only. The data were calculated as follows:

$$\% \text{ Effect } (E) = \frac{MRT^* \text{ (Treated)} - MRT \text{ (Control} \times 100)}{10 - MRT \text{ (Control)}}$$

$$\% \text{ Antagonism} = \frac{E(\text{morphine controls}) - E(\text{drug treated}) \times 100}{E(\text{morphine control})}$$

*MRT is defined as mean reaction time.

The data were plotted on log-probit paper and $AD_{50}$ values, i.e., the dose required to inhibit the morphine effect by 50% within 95% condidence limits, were determined by the method of Litchfield and Wilcoxon.

The results of this pharmacological evaluation are set out in Table I where CPM stands for cyclopropylmethyl, CBM stands for cyclobutylmethyl and IA means inactive at the dose indicated.

TABLE I

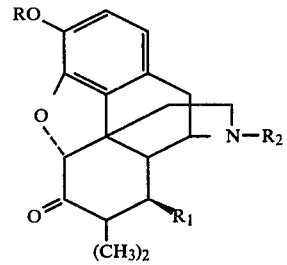

(CH₃)₂

| Compound | Ex. | R | $R_1$ | $R_2$ | $ED_{50}$ (mg/kg) | $AD_{50}$ (mg/kg) |
|---|---|---|---|---|---|---|
| TR-5385 | VIIIA | $CH_3$ | H | CPM | 1.93 | 2.48 |
| TR-5458 | VIIIB | $CH_3$ | $CH_3$ | CPM | >10 | 2.80 |
| TR-5443 | VIIIC | $CH_3$ | $CH_2CH_3$ | CPM | IA10 | >10 |
| TR-5386 | VIIID | $CH_3$ | H | CBM | IA10 | >10 |
| TR-5462 | VIIIE | H | $CH_3$ | CBM | 6.80 | 1.84 |
| TR-5444 | VIIIF | $CH_3$ | $CH_2CH_3$ | CBM | >10 | >10 |
| TR-5388 | IXC | H | H | CPM | IA10 | 0.42 |
| TR-5461 | IXD | H | $CH_3$ | CPM | IA10 | 0.17 |
| TR-5449 | IXE | H | $CH_2CH_3$ | CPM | IA10 | 1.51 |
| TR-5390 | IXF | H | H | CBM | 0.91 | >10 |
| TR-5459 | IXG | $CH_3$ | $CH_3$ | CBM | >10 | >10 |
| TR-5450 | IXH | H | $CH_2CH_3$ | CBM | 8.80 | 1.33 |

The compounds of the present invention form pharmacologically acceptable addition salts with organic and inorganic acids. Typical acid addition salts are the tartrate, hydrobromide, hydrochloride and maleate. The hydrochloride is preferred.

Those compounds which are pure analgesics are useful for relieving moderate to severe pain in an individual for whom such therapy is indicated whereas those compounds which have been found to be narcotic antagonists are useful for treating drug dependence in an individual for whom such therapy is indicated. Those compounds which are mixed analgesics/narcotic antagonists are useful for treating pain without the liability of drug dependence.

The term "individual" means a human being or an experimental animal that is a model for a human being. The dose to be administered to achieve the desired result, i.e., the effective dose, may vary from individual to individual but is readily determined by one skilled in the art without undue experimentation.

The compounds of the present invention may be administered by known, conventional methods of therapeutic administration such as intravenous, parenteral, buccal, rectal or oral. Dose forms for the administration of these compounds can be prepared by methods recognized in the pharmaceutical sciences.

What is claimed is:

1. A 7,7-ditosyloxymethyl-4,5α-epoxy-3-methoxy-17-methyl-morphinan-6β-ol of the formula:

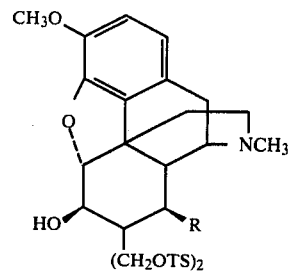

where R is H, $CH_3$ or $CH_2CH_3$.

2. A compound as defined in claim 1 wherein R is H.

3. A compound as defined in claim 1 wherein R is $CH_3$.

4. A compound as defined in claim 1 wherein R is $CH_2CH_3$.

* * * * *